United States Patent
Kingston et al.

(10) Patent No.: US 10,078,057 B2
(45) Date of Patent: Sep. 18, 2018

(54) DATA PROCESSING IN A TOMOGRAPHIC IMAGING APPARATUS

(71) Applicant: FEI Company, Hillsboro, OR (US)

(72) Inventors: Andrew Kingston, Kambah (AU); Shane Latham, Griffith (AU); Adrian Sheppard, Fisher (AU); Glenn Myers, Waramanga (AU); Benoit Recur, Turner (AU); Heyang Li, Harrison (AU)

(73) Assignee: FEI Company, Hillsboro, OR (US)

( * ) Notice: Subject to any disclaimer, the term of this patent is extended or adjusted under 35 U.S.C. 154(b) by 49 days.

(21) Appl. No.: 15/215,341

(22) Filed: Jul. 20, 2016

(65) Prior Publication Data
US 2017/0059493 A1 Mar. 2, 2017

(30) Foreign Application Priority Data
Sep. 2, 2015 (EP) .................... 15183475

(51) Int. Cl.
*G06K 9/00* (2006.01)
*G01N 23/046* (2018.01)
(Continued)

(52) U.S. Cl.
CPC .......... *G01N 23/046* (2013.01); *G06T 11/006* (2013.01); *H01J 37/26* (2013.01);
(Continued)

(58) Field of Classification Search
CPC ........... G01N 23/046; G01N 23/20058; G01N 23/2251; G01N 2223/419;
(Continued)

(56) References Cited

U.S. PATENT DOCUMENTS

| 6,240,157 B1 | 5/2001 | Danielsson | |
| 8,008,633 B2 * | 8/2011 | Fujiyoshi | H01J 37/20 250/306 |

(Continued)

FOREIGN PATENT DOCUMENTS

WO 2015125086 A1 8/2015

OTHER PUBLICATIONS

Bleuet, P. et al., "SEM-based system for 100nm x-ray tomography for the analysis of porous silicon," Proceedings of SPIE, Sep. 11, 2014, vol. 9212, pp. 92120Z-1 to 92120Z-9.
(Continued)

*Primary Examiner* — Jose Couso
(74) *Attorney, Agent, or Firm* — Scheinberg & Associates, P.C.; Michael O. Scheinberg

(57) ABSTRACT

A method of investigating a specimen using a tomographic imaging apparatus, by performing, in multiple iterations, the following steps:
  (i) Using a Back Projection technique to produce an initial tomogram from a set of initial images;
  (ii) Subjecting said initial tomogram to a mathematical filtering operation, thereby producing an adjusted tomogram;
  (iii) Using a Forward Projection technique on said adjusted tomogram to dissociate it into a set of calculated images;
  (iv) Repeating steps (i)-(iii) until said calculated images satisfy an acceptance criterion.

20 Claims, 3 Drawing Sheets

Figure 1:
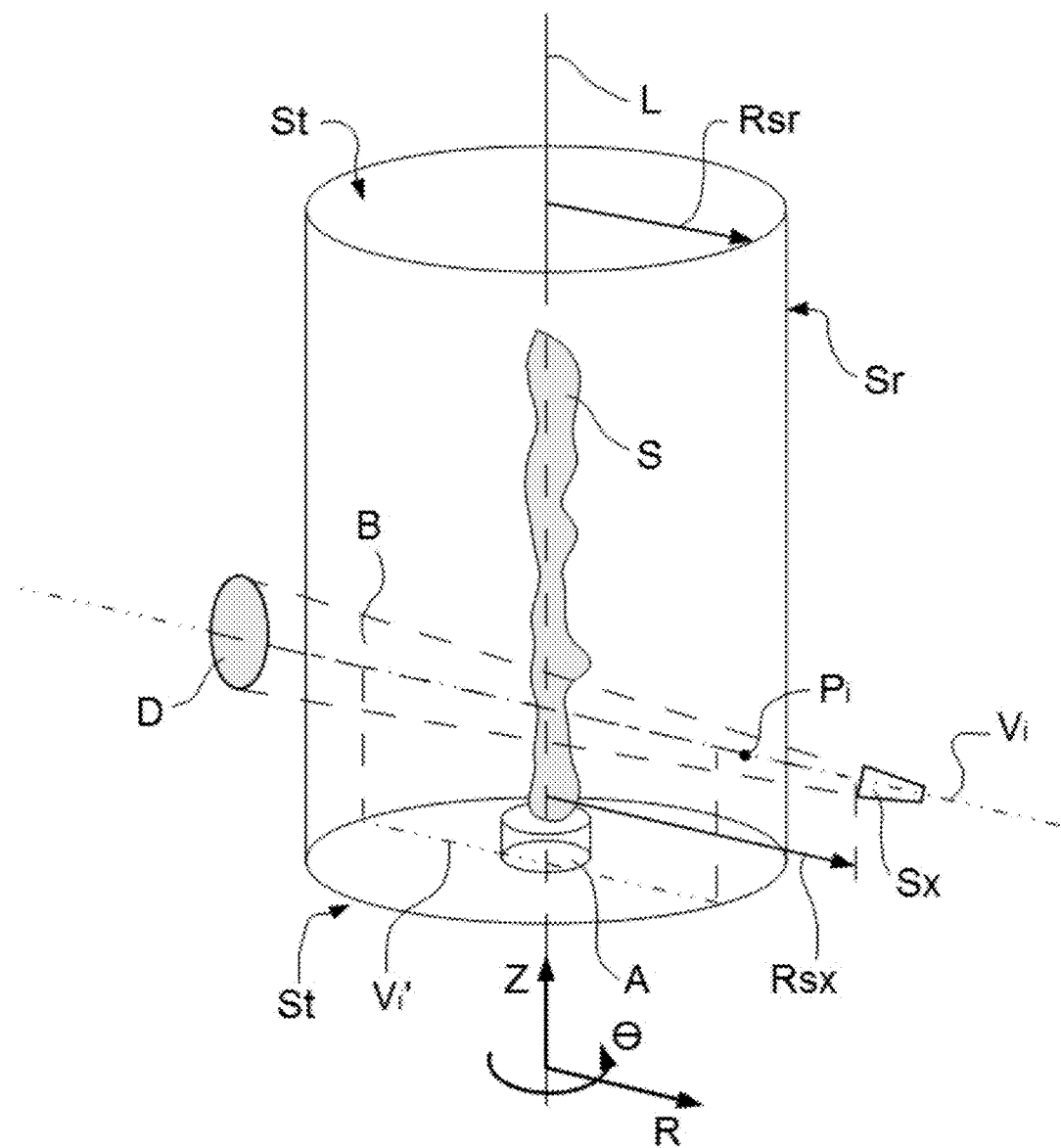

(51) Int. Cl.
*H01J 37/26* (2006.01)
*G06T 11/00* (2006.01)

(52) U.S. Cl.
CPC . *G01N 2223/401* (2013.01); *G01N 2223/418* (2013.01); *G01N 2223/419* (2013.01)

(58) Field of Classification Search
CPC ....... G01N 2223/418; G01N 2223/102; G01N 2223/309; G01N 2223/32; G01N 2223/3306; G01N 2223/612; G01N 15/1468; G01N 15/1475; G01N 2015/1445; G01N 29/0672; G01N 2021/1787; G01N 2021/0346; H01J 37/26; H01J 37/20; H01J 37/21; H01J 37/22; H01J 37/28; H01J 37/222; H01J 37/244; H01J 37/265; H01J 37/395; H01J 2237/2802; H01J 2237/20207; H01J 2237/226; H01J 2237/2611; H01J 2237/20228; H01J 2237/20235; H01J 2237/20264; H01J 2237/20285; H01J 2237/21; H01J 2237/24485; H01J 2237/24585; H01J 2237/26; H01J 2237/2807; G06T 11/006; G06T 11/005; G06T 11/003; G06T 2211/40; G06T 2211/421; G06T 2211/424; G06T 2211/412; G06T 2211/416; G06T 2207/10076–2207/10108; A61B 6/027; A61B 3/102; A61B 5/0033; A61B 5/0035; A61B 5/0073; A61B 5/0522; A61B 5/0536; A61B 6/03–6/037; A61B 8/13–8/15; A61B 2090/3735–2090/3762; Y10S 128/922; Y10S 378/901; G06K 9/0057

See application file for complete search history.

(56) References Cited

U.S. PATENT DOCUMENTS

| | | | |
|---|---|---|---|
| 9,336,612 B2* | 5/2016 | Brown | G06T 5/50 |
| 2005/0152590 A1 | 7/2005 | Thieret et al. | |
| 2012/0001068 A1 | 1/2012 | He et al. | |
| 2014/0070095 A1 | 3/2014 | Schoenmakers et al. | |
| 2014/0145077 A1 | 5/2014 | Schoenmakers et al. | |
| 2015/0069231 A1 | 3/2015 | Luecken et al. | |
| 2016/0350945 A1* | 12/2016 | Song | G06T 11/006 |

OTHER PUBLICATIONS

Nakajima, M. et al., "Micro-CT imaging of Caenorhabditis elegans under Environmental-SEM," Proceedings of the 2013 International Symposium on Micro-Nanomechatronics and Human Science (MHS), Nov. 10, 2013, pp. 1-2.
"Cone Beam Computed Tomography", Wikipedia, Retrieved from the Internet Aug. 4, 2016, from https://en.wikipedia.org/wiki/Cone_beam_computed_tomography, 8 pages.
"Electron Microscope", Wikipedia, Retrieved from the Internet Oct. 15, 2015, http://en.wikipedia.org/wiki/Electron_microscope, 11 pages.
"Focused Ion Beam", Wikipedia, Retrieved from the Internet Aug. 4, 2016, https://en.wikipedia.org/wiki/Focused_ion_beam, 7 pages.
"Nanotomography", Wikipedia, Retrieved from the Internet Aug. 4, 2016, from https://en.wikipedia.org/wiki/Nanotomography, 1 page.
"Scanning Electron Microscope", Wikipedia. Retrieved from the Internet Aug. 4, 2016, http://en.wikipedia.org/wiki/Scanning_electron_microscope, 23 pages.
"Scanning Helium Ion Microscope", Wikipedia, Retrieved from the Internet on Aug. 4, 2016, http://en.wikipedia.org/wiki/Scanning_Helium_Ion_Microscope, 2 pages.
"Scanning Transmission Electron Microscopy", Wikipedia, Retrieved from the Internet Aug. 4, 2016, http://en.wikipedia.org/wiki/Scanning_transmission_electron_microscopy, 5 pages.
"Spiral Computed Tomography", Wikipedia, Retrieved from the Internet Aug. 4, 2016, https://en.wikipedia.org/wiki/Spiral_computed_tomography, 2 pages.
"Transmission Electron Microscopy", Wikipedia, Retrieved from the Internet http://en.wikipedia.org/wiki/Transmission_electron_microscopy, Aug. 4, 2016, 23 pages.
"X-ray microtomography", Wikipedia, Retrieved from the Internet https://en.wikipedia.org/wiki/X-ray_microtomography, Aug. 4, 2016, 5 pages.
Abbas, Sajid et al., "Effects of sparse sampling schemes on image quality in low-dose CT," Medical Physics, Nov. 2013, pp. 111915-1-111915-6 , vol. 40, Issue 11.
Escovitz W.H. et al, Scanning Transmission Ion Microscope with a Field Ion Source, Retrieved from the internet Oct. 15, 2015; http://www.pnas.org/content/72/5/1826.full.pdf, 3 pages.
Neuser, E., et al. "NanoCT® Visualizing internal 3D structures with submicrometer resolution", DIR 2007, 18 p, vol. 39 Issue 41, International symposium on digital industrial radiology and computed tomography, France.
Varentsov, D., et al. "First biological images with high-energy proton microscopy", Apr. 1, 2012, http://www.ncbi.nlm.nih.gov/pubmed/22472444, pp. 208-213.

* cited by examiner

DATA PROCESSING IN A TOMOGRAPHIC IMAGING APPARATUS

The invention relates to a method of investigating a specimen using a tomographic imaging apparatus comprising:
- A specimen holder, for holding the specimen;
- A source, for producing a beam of radiation that can be directed at the specimen;
- A detector, for detecting a flux of radiation transmitted through the specimen from the source;
- A stage apparatus, for producing relative motion (positioning) of the source with respect to the specimen, so as to allow the source and detector to image the specimen along a series of different viewing axes;
- A processing apparatus, for performing a mathematical reconstruction step whereby output from the detector is compiled into a tomographic image of at least part of the specimen, The invention also relates to a tomographic imaging apparatus that can be used in performing such a method.

The invention further relates to a charged-particle microscope provided with such a tomographic imaging apparatus.

In tomographic imaging (also referred to as Computed Tomography (CT)) as referred to above, the source and (diametrically opposed) detector are used to look through the specimen along different lines of sight (viewing axes), so as to acquire penetrative observations of the specimen from a variety of perspectives; these are then used as input to a mathematical procedure that produces a reconstructed "volume image" of (part of) the (interior of) the specimen. In order to achieve a series of different lines of sight as alluded to here, one can, for example, choose to:
(a) Keep the source and detector static and move the specimen relative to them;
(b) Keep the specimen static and move the source relative to it. In this case, one can elect to:
 Move the detector in synchronization with the source; or
 Embody the detector as a (static) array of sub-detectors, with positions matched to correspond to the different positions to be assumed by the source.

Regardless of whether the source or specimen is moved, it is possible to describe their relative motion using (for example) a specimen-centric coordinate system/reference frame. The beam of radiation that traverses the specimen can, for example, be regarded as being cone-like (thus yielding so-called cone beam tomography) or resembling a segment of a disc (thus yielding so-called fan beam tomography), depending on the geometry/shape that the detector "presents" to the source; a parallel/collimated beam is also possible. The "viewing axis" alluded to here can be regarded as corresponding to an "optical axis" along which the beam (from source through specimen to detector) propagates; it basically corresponds to the position of a central/median/core ray in that beam. In order to achieve sufficient sample penetration, the employed radiation will generally comprise X-rays.

Tomographic imaging as referred to here can be performed using a standalone apparatus, which is conventionally the case in medical imaging applications, for example, where the specimen (e.g. a human or animal) is macroscopic. Standalone CT tools are also available for performing so-called "micro CT", in which a micro-focused source is used to image microscopic specimens, e.g. in geology/petrology, biological tissue studies, etc. Continuing this drive toward ever-greater resolution, so-called "nano CT" instruments have also been developed; these may be standalone tools, but, for example, they may also be embodied as (add-on) modules for (a vacant vacuum/interface port of) a charged-particle microscope (CPM), in which case the CPM's charged-particle beam is used to irradiate a metal target, causing production of the Bremsstrahlung X-rays used to perform the desired tomography (see FIG. 3, for example). More information on (some) of these topics can, for example, be gleaned from the following references:
 https://en.wikipedia.org/wiki/X-ray_microtomography
 https://en.wikipedia.org/wiki/Nanotomography
 http://www.ndt.net/article/dir2007/papers/24.pdf It should be noted that, as referred to here in the context of a CPM, the phrase "charged particle" should be broadly construed as encompassing:
 Electrons, as in the case of a Transmission Electron Microscope (TEM), Scanning Electron Microscope (SEM), and Scanning Transmission Electron Microscope (STEM), for instance. See, for example, the following references:
  http://en.wikipedia.org/wiki/Electron_microscope
  http://en.wikipedia.org/wiki/Scanning_electron_microscope
  http://en.wikipedia.org/wiki/Transmission_electron_microscopy
  http://en.wikipedia.org/wiki/Scanning_transmission_electron_microscopy
 Ions, which may be positive (e.g. Ga or He ions) or negative. Such ion beams can be used for imaging purposes, but they are also often used for surface modification purposes, e.g. as in the case of Focused Ion Beam (FIB) milling, Ion-Beam-Induced Deposition (IBID), Ion-Beam-Induced Etching (IBIE), etc. See, for example, the following references:
  https://en.wikipedia.org/wiki/Focused_ion_beam
  http://en.wikipedia.org/wiki/Scanning_Helium_Ion_Microscope
  W. H. Escovitz, T. R. Fox and R. Levi-Setti, *Scanning Transmission Ion Microscope with a Field Ion Source*, Proc. Nat. Acad. Sci. USA 72(5), pp 1826-1828 (1975).
 Other charged particles, such as protons and positrons, for instance. See, for example, the following reference:
  http://www.ncbi.nlm.nih.gov/pubmed/22472444

It should also be noted that, in addition to imaging and/or surface modification, a charged particle beam in a CPM may also have other functionalities, such as performing spectroscopy, examining diffractograms, etc.

As regards the specimen/source relative motion employed to achieve different lines of sight/viewing axes [data acquisition step], use is conventionally made of:
 A circular scan, in which the source follows a planar orbit about the specimen, and images are captured at a relatively high sampling rate (i.e. quasi-continuously) along this orbit. This type of scan can be applied in situations where only a relatively thin "slice" of a specimen has to be imaged, e.g. when making a cone beam CT scan of human dentition. See, for example, the following reference:
  https://en.wikipedia.org/wiki/Cone_beam_computed_tomography
 A helical scan, in which the source follows a coil-like (spiral) path about a (longitudinal) axis of the specimen, and images are again captured at a relatively high sampling rate (i.e. quasi-continuously) along this path. This type of scan can be applied in situations where a relatively elongated portion of a specimen has to be imaged, e.g. when making a CT scan of (a portion of)

a human vertebral column. It is typically achieved by combining circular motion (e.g. of the source) and concurrent translational motion (e.g. of the specimen). See, for example, the following reference: https://en.wikipedia.org/wiki/Spiral_computed_tomography As an alternative to conventional curvilinear scan loci—such as the circular/spiral scan paths just referred to—one can, for example, also make use of a lattice-like data acquisition locus, e.g. as set forth in co-pending European Patent Application EP15181202.1 (FNL1515).

The "raw" imaging data obtained in the data acquisition step can subsequently be used as a basis for tomogram construction [data processing step]. For example:

A common technique used in tomographic reconstruction is so-called Back Projection (BP). BP is a procedure whereby an image of a specimen, taken along a given viewing axis, is back-projected (smeared out) along that viewing axis, through the specimen. When this is done for several appropriately chosen viewing axes, the various back-projected images will intersect and form a blurry image at the location of the specimen, which blurry image then forms a basis for subsequent reconstructive processing. This basic BP technique can, if desired, be modified by applying an appropriate filter to the image data prior to the tomographic reconstruction process, resulting in a procedure that is referred to as Filtered Back Projection (FBP).

As an alternative and/or supplement to the use of BP, one can instead make use of an iterative reconstruction technique to produce a tomographic image. Examples of such iterative techniques include SIRT (Simultaneous Iterative Reconstruction Technique), ART (Algebraic Reconstruction Technique), DART (Discrete ART), SART (Simultaneous ART), etc. Such iterative techniques (generally) have the advantage of being less noise-sensitive, and of allowing (physical) constraints to be applied to the reconstruction process; however, because they employ several iterations, they tend to be more time-consuming, and to converge relatively slowly.

Although prior-art data processing techniques such as those set forth above have produced tolerable results up to now, the current inventors have worked extensively to provide an innovative alternative to conventional approaches. The results of this endeavor are the subject of the current invention.

It is an object of the invention to provide an innovative tomographic imaging technique. More specifically, it is an object of the invention that this technique should employ a radically different data processing strategy as compared to known techniques.

These and other objects are achieved in a method as set forth in the opening paragraph above, which method is characterized in that said reconstruction step is performed in multiple iterations, which comprise the following steps:

(i) Using a Back Projection technique to produce an initial tomogram from a set of initial images;
(ii) Subjecting said initial tomogram to a mathematical filtering operation, thereby producing an adjusted tomogram;
(iii) Using a Forward Projection technique on said adjusted tomogram to dissociate it into a set of calculated images;
(iv) Repeating steps (i)-(iii) until said calculated images satisfy an acceptance criterion.

In each repeat iteration, the input to step (i) derives from the output from previous step (iii).

The current invention differs fundamentally from the prior art in that it uses an iterative reconstruction scheme in which, per iteration, a mathematical filter is applied (in reconstruction space) in order to manipulate the tomographic data—with the ultimate aim of allowing acceleration of the convergence process to a desired result, while simultaneously providing an extra means of adjusting the quality of the final tomogram. On a more abstract level, the employed filtering can be used to accentuate certain (higher) frequencies and suppress other (lower) frequencies in Fourier space, which can be used to considerably sharpen back-projected imagery before a subsequent reconstruction iteration. Such filtering can, for example, be performed using an appropriately chosen/regularized (space-invariant) Laplace operator or convolution operator, for instance. By sub-dividing the reconstructive process into iterations, the exact form of the applied filter does not have to be the same for all iterations/steps, but can instead be optimized (fine-tuned) on a step-by-step basis. The "acceptance criterion" referred to here may, for example, be a pre-defined threshold value of a metric that compares/correlates the calculated images to progenitor initial images/reference images; the skilled artisan will be familiar with various mathematical divergence measures that can be used in this regard. The "Forward Projection" alluded to here can also be referred to as "re-projection", and may be seen as being the opposite (mathematical adjoint operation) of "Back Projection".

A particularly effective embodiment of the present invention can be achieved if the basic "filtered iterative reconstruction" technique referred to in the previous paragraph is performed in a "multi-grid" manner, whereby one starts with a relatively coarse-grid (low-resolution) tomogram and progresses iteratively through successively finer grids (higher resolutions). Such an approach can result in significantly increased computational efficiency since, as a rule of thumb, coarsening data by a factor of two tends to reduce computation time by a factor of sixteen. The relatively coarse initial tomogram can, for example, be achieved by:

Using a coarse data acquisition strategy, with a relatively low density of viewing axes; or
Applying downsampling/binning to relatively fine acquisition data, to deliberately blur/coarsen it.

The filtering that characterizes the current invention can be used to de-blur an initial tomogram, thus producing an improved "update" tomogram that can serve as a basis for the next iteration of the reconstruction process. The same approach can, if desired, also be used to deliberately decrease the resolution of a successor tomogram relative to a progenitor tomogram, so as to perform intentional blurring.

A special embodiment of the current invention comprises the following additional steps:

Comparing given calculated images to corresponding initial images, and calculating a set of transformations necessary to map the former onto the latter;
Using said set of transformations to modify the initial images used in step (i) of a subsequent iteration.

Such an embodiment may be regarded as being a hybrid of the current invention and the invention set forth in co-pending European Patent Application EP15182129.5 (FNL1516), in that it combines/intermixes the following activities:

Mathematical filtering of tomograms in mathematical/reconstruction space;

Geometrical manipulation of images in physical/image space.

In such an approach, the iterative reconstruction process is "tweaked from both sides", to achieve an even better result.

The invention will now be elucidated in more detail on the basis of exemplary embodiments and the accompanying schematic drawings, in which:

FIG. 1 renders a perspective view of a specimen undergoing tomographic imaging, and serves to explain certain (reference) geometric aspects of the current invention.

Figure 2:
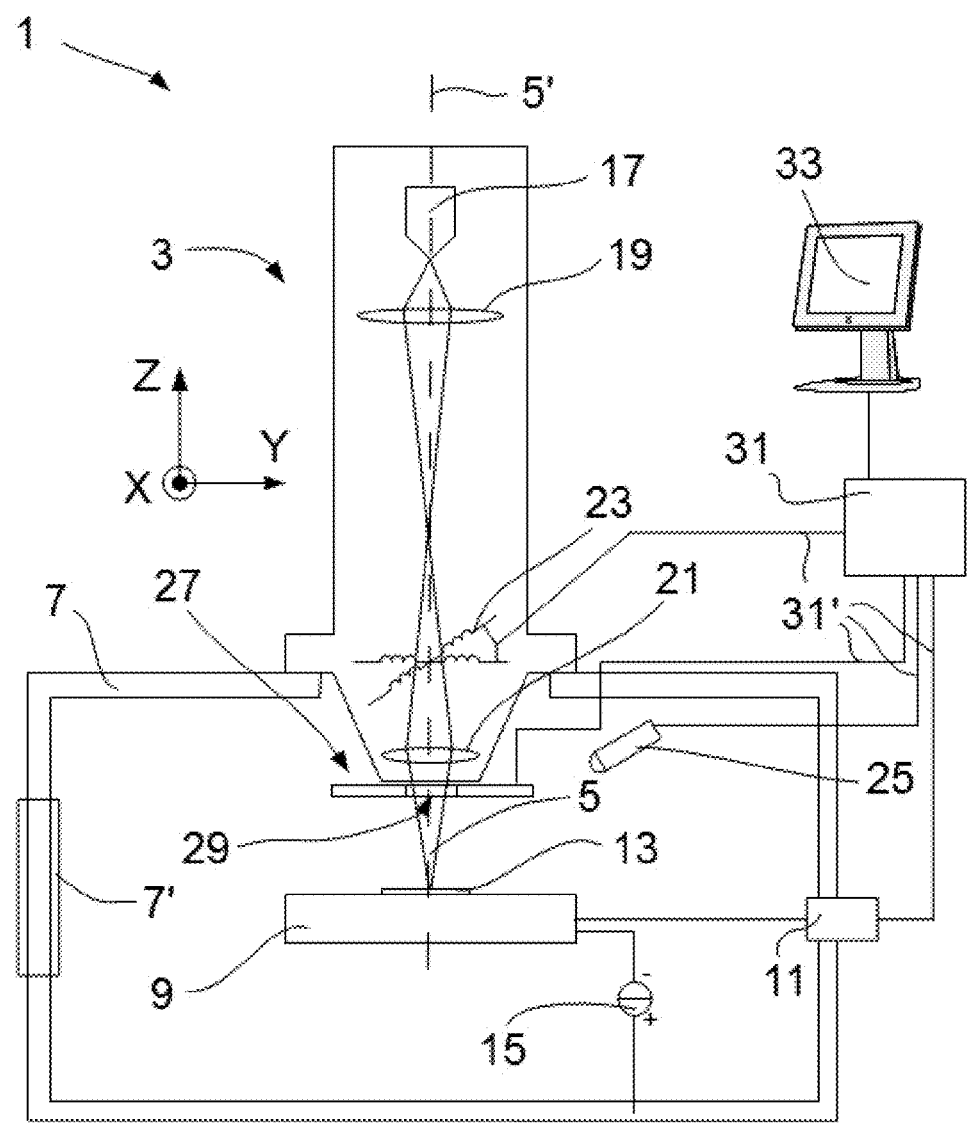

FIG. 2 renders a longitudinal cross-sectional elevation of a particular type of CPM in which an embodiment of the current invention can be carried out using a CT module.

Figure 3:
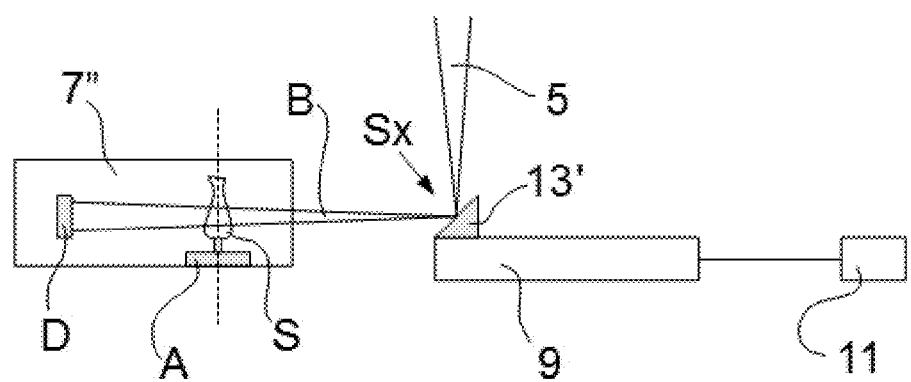

FIG. 3 illustrates a CT module suitable for use in a CPM such as that shown in FIG. 2.

EMBODIMENT 1

FIG. 1 renders a perspective view of a specimen S undergoing tomographic imaging, and serves to explain certain (reference) geometric aspects of the current invention. In the Figure, an elongated specimen S (which may be macroscopic, micron-scale, or nanometer-scale, for example) has an associated longitudinal axis L. A radiation source Sx produces a beam B of radiation (typically X-rays) that propagates along an axis $V_i$, which may be regarded as a viewing axis or line of sight. As here illustrated, $V_i$ is substantially normal to longitudinal axis L. Having traversed a portion of the specimen S, the beam B impinges upon a (diametrically opposed) detector D, which may, for example, be a Silicon Drift Detector (SDD), Silicon Lithium (Si(Li)) detector, or other suitable detector. The beam B may be regarded as being (for example) cone- or fan-shaped, depending on the effective shape that the detector D "presents" to the source Sx. The detector D forms an electronic image of said portion of the specimen S, which can be stored in an electronic memory. This procedure is then repeated for a series of different viewing axes $V_i$, allowing the specimen S to be viewed along different lines of sight; thereafter, the various images acquired in this manner are used as input to a mathematical reconstruction procedure to produce a tomogram. The various viewing axes $V_i$ are achieved by employing a stage apparatus to produce relative motion between the source Sx and specimen S, e.g. by producing translational/rotational motion of the source Sx/detector D and/or the specimen S in a pre-determined way. Such stage apparatus may, for example, comprise one or more linear motors, piezoelectric actuators, stepper motors, voice coil motors, pneumatic/hydraulic actuators, etc., and can readily be tailored by the skilled artisan to suit the needs of a given setup. In the specific embodiment depicted here, stage apparatus A can translate/rotate specimen S relative to source Sx/detector D.

Also shown in the Figure is a virtual reference surface Sr, which, in this case, is a cylindrical surface whose cylindrical axis coincides with longitudinal axis L. This reference surface Sr has a radius Rsr, chosen to be less than or equal to the distance Rsx of the source Sx from the axis L. The viewing axis $V_i$ intersects this reference surface Sr at intersection point $P_i$. Note that, if viewing axis $V_i$ is projected linearly along L, it will coincide with a diameter of a virtual disc-shaped terminal surface St at butt ends of the surface Sr. Associated with the reference surface Sr is a cylindrical coordinate system $(R, \theta, Z)$. The set $\{P_i\}$ of intersection points $P_i$ corresponding to the abovementioned series of viewing axes $V_i$ can be regarded as representing a "data acquisition locus", such as the circular or helical scanning path referred to above, or the lattice-like locus set forth in aforementioned patent application EP15181202.1, for example.

EMBODIMENT 2

FIG. 2 is a highly schematic depiction of an embodiment of a CPM 1 that can be used in conjunction with the present invention; more specifically, it shows an embodiment of a SEM—though, in the context of the current invention, it could just as validly be an ion-based microscope, for example, or a TEM, for instance. The microscope 1 comprises a particle-optical column/illuminator 3, which produces a beam 5 of charged particles (in this case, an electron beam) that propagates along a particle-optical axis 5'. The particle-optical column 3 is mounted on a vacuum chamber 7, which comprises a specimen holder 9 and associated stage/actuator 11 for holding/positioning a specimen 13. The vacuum chamber 7 is evacuated using vacuum pumps (not depicted). With the aid of voltage source 15, the specimen holder 9, or at least the specimen 13, may, if desired, be biased (floated) to an electrical potential with respect to ground.

The particle-optical column 3 comprises an electron source 17 (such as a Schottky emitter), (electrostatic/magnetic) lenses 19, 21 (in general, more complex in structure than the schematic depiction here) to focus the electron beam 5 onto the specimen 13, and a deflection unit 23 to perform beam deflection/scanning of the beam 5. When the beam 5 impinges on/is scanned across the specimen 13, it will precipitate emission of various types of "stimulated" radiation, such as backscattered electrons, secondary electrons, X-rays and cathodoluminescence (infra-red, visible and/or ultra-violet photons); one or more of these radiation types can then be sensed/recorded using one or more detectors, which may form an image, spectrum, diffractogram, etc., typically by assembling a "map" (or "matrix") of detector output as a function of scan position on the specimen. The present Figure shows two such detectors, 25, 27, which may, for example, be embodied as follows:

Detector 25 may, for example, be an electron detector (such as an Solid State Photo-Multiplier), X-ray detector (such as an SDD or Si(Li) sensor) or a light detector (such as a photodiode).

Detector 27 is a segmented electron detector, comprising a plurality of independent detection segments (e.g. quadrants) disposed about a central aperture 29 (allowing passage of the beam 5). Such a detector can, for example, be used to investigate (the angular dependence of) a flux of output (secondary or backscattered) electrons emerging from the specimen 13.

These are just examples, and the skilled artisan will understand that other detector types, numbers and geometries/configurations are possible.

The microscope 1 further comprises a controller/computer processing unit 31 for controlling inter alia the lenses 19 and 21, the deflection unit 23, and detectors 25, 27, and displaying information gathered from the detectors 25, 27 on a display unit 33 (such as a flat panel display); such control occurs via control lines (buses) 31'. The controller 31 (or another controller) can additionally be used to perform various mathematical processing, such as combining, integrating, subtracting, false colouring, edge enhancing, and other processing known to the skilled artisan. In addition, automated recognition processes (e.g. as used for particle analysis) may be included in such processing.

Also depicted is a vacuum port 7', which may be opened so as to introduce/remove items (components, specimens) to/from the interior of vacuum chamber 7, or onto which, for example, an ancillary device/module may be mounted (not depicted). A microscope 1 may comprise a plurality of such ports 7', if desired.

In the context of the current invention, the microscope 1 can also comprise an in situ CT module 7" as shown in FIG. 3. In this figure, the CPM's specimen holder 9 has been provided with a metal target 13', which is positioned (using actuator 11) so that electron beam 5 impinges upon it, thus producing Bremsstrahlung X-rays in a variety of directions. The Figure shows a beam B of such X-rays that propagate to one side from target 13' (effective source Sx) into module 7", where they pass through a specimen S and impinge upon a detector D: compare to FIG. 1. The specimen S is mounted on a stage apparatus A that allows the specimen S to be positioned/moved (typically translated and rotated) relative to the source Sx.

Such a CT module 7" may be permanently present (ab initio) in the vacuum enclosure 7, or it may be an add-on module that can be mounted (post-manufacture of the CPM 1) on/within a spare vacuum port 7', for example.

The invention claimed is:

1. A method of investigating a specimen using a tomographic imaging apparatus, the tomographic imaging apparatus comprising:
    a specimen holder, for holding the specimen;
    a source, for producing a beam of radiation that can be directed at the specimen;
    a detector, for detecting a flux of radiation transmitted through the specimen from the source;
    a stage apparatus, for producing relative motion of the source with respect to the specimen, so as to allow the source and detector to image the specimen along a series of different viewing axes; and
    a processing apparatus, for performing a mathematical reconstruction step whereby output from the detector is compiled into a tomographic image of at least part of the specimen, and
    the method comprising:
    performing multiple iterations of the mathematical reconstruction step, each iteration comprising:
        using a back projection technique to produce an initial tomogram from a set of initial images,
        subjecting said initial tomogram to a mathematical filtering operation, thereby producing an adjusted tomogram, and
        using a forward projection technique on said adjusted tomogram to dissociate it into a set of calculated images; and
    terminating the iteration of the mathematical reconstruction step when said calculated images satisfy an acceptance criterion.

2. A method according to claim 1, wherein said mathematical filtering operation serves to manipulate a frequency spectrum of said initial tomogram in Fourier space.

3. A method according to claim 1, wherein said mathematical filtering operation employs a space-invariant filter.

4. A method according to claim 1, wherein, for at least one iteration:
    the initial tomogram has a first resolution; and
    the adjusted tomogram has a second resolution, different to said first resolution.

5. A method according to claim 4, wherein said first resolution is lower than said second resolution.

6. A method according to claim 4, wherein said first resolution is higher than said second resolution.

7. A method according to claim 1, comprising the following additional steps:
    comparing given calculated images to corresponding initial images, and calculating a set of transformations necessary to map the former onto the latter; and
    using said set of transformations to modify the initial images used in the production of an initial tomogram of a subsequent iteration.

8. A method according to claim 1, wherein said relative motion of the source with respect to the specimen traces out a locus selected from the group consisting of a substantially circular curve, a substantially helical curve, and combinations thereof.

9. A method according to claim 1, comprising:
    considering a virtual reference surface that surrounds the specimen and is substantially centered thereon;
    considering an incoming point of intersection of each of said viewing axes with this reference surface, thereby generating a set of such intersection points corresponding to said series of viewing axes; and
    choosing discrete viewing axes in said series so as to cause said set to comprise a two-dimensional lattice of points located areally on said reference surface in a substantially uniform distribution.

10. A tomographic imaging apparatus comprising:
    a specimen holder, for holding a specimen;
    a source, for producing a beam of radiation that can be directed at the specimen;
    a detector, for detecting a flux of radiation transmitted through the specimen from the source;
    a stage apparatus, for producing relative motion of the source with respect to the specimen, so as to allow the source and detector to image the specimen along a series of different viewing axes; and
    a processing apparatus, for performing a mathematical reconstruction step whereby output from the detector is compiled into a tomographic image of at least part of the specimen,
    wherein said processing apparatus is configured to:
    perform multiple iterations of the mathematical reconstruction step, each iteration comprising:
        using a back projection technique to produce an initial tomogram from a set of initial images,
        subjecting said initial tomogram to a mathematical filtering operation, thereby producing an adjusted tomogram, and
        using a forward projection technique on said adjusted tomogram to dissociate it into a set of calculated images; and
    terminate the iteration of the mathematical reconstruction step when said calculated images satisfy an acceptance criterion.

11. A charged-particle microscope comprising a tomographic imaging apparatus as claimed in claim 10.

12. A method according to claim 2, wherein said mathematical filtering operation employs a space-invariant filter.

13. A method according to claim 2, wherein, for at least one iteration:
    the initial tomogram has a first resolution; and
    the adjusted tomogram has a second resolution, different to said first resolution.

14. A method according to claim 13, wherein said first resolution is lower than said second resolution.

15. A method according to claim 13, wherein said first resolution is higher than said second resolution.

16. A method according to claim 3, wherein, for at least one iteration:
  the initial tomogram has a first resolution; and
  the adjusted tomogram has a second resolution, different to said first resolution.

17. A method according to claim 2, wherein said relative motion of the source with respect to the specimen traces out a locus selected from the group consisting of a substantially circular curve, a substantially helical curve, and combinations thereof.

18. A method according to claim 2, comprising:
  considering a virtual reference surface that surrounds the specimen and is substantially centered thereon;
  considering an incoming point of intersection of each of said viewing axes with this reference surface, thereby generating a set of such intersection points corresponding to said series of viewing axes; and
  choosing discrete viewing axes in said series so as to cause said set to comprise a two-dimensional lattice of points located areally on said reference surface in a substantially uniform distribution.

19. A method according to claim 3, comprising:
  considering a virtual reference surface that surrounds the specimen and is substantially centered thereon;
  considering an incoming point of intersection of each of said viewing axes with this reference surface, thereby generating a set of such intersection points corresponding to said series of viewing axes; and
  choosing discrete viewing axes in said series so as to cause said set to comprise a two-dimensional lattice of points located areally on said reference surface in a substantially uniform distribution.

20. The method of claim 1 in which using a back projection technique to produce an initial tomogram from a set of initial images comprises using a back projection technique to produce an initial tomogram from a set of initial images acquired along a series of viewing axes using one or more detectors.

* * * * *